United States Patent
Lyden et al.

(10) Patent No.: US 10,682,522 B2
(45) Date of Patent: *Jun. 16, 2020

(54) IMPLANTABLE MEDICAL DEVICE INCLUDING EDDY CURRENT REDUCING BATTERY

(71) Applicant: Cardiac Pacemakers, Inc., St. Paul, MN (US)

(72) Inventors: Michael J. Lyden, Shoreview, MN (US); Michael J. Root, Lino Lakes, MN (US); Kurt E. Koshiol, Minnetonka, MN (US); Lisa B. Schmalhurst, Bellevue, WA (US); Yingbo Li, Woodbury, MN (US); Masoud Ameri, Maple Plain, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/253,394

(22) Filed: Jan. 22, 2019

(65) Prior Publication Data
US 2019/0151669 A1 May 23, 2019

Related U.S. Application Data

(63) Continuation of application No. 14/445,864, filed on Jul. 29, 2014, now Pat. No. 10,220,216, which is a
(Continued)

(51) Int. Cl.
*H01M 4/66* (2006.01)
*A61N 1/378* (2006.01)
(Continued)

(52) U.S. Cl.
CPC ............. *A61N 1/3787* (2013.01); *A61N 1/08* (2013.01); *A61N 1/375* (2013.01); *A61N 1/378* (2013.01);
(Continued)

(58) Field of Classification Search
None
See application file for complete search history.

(56) References Cited

U.S. PATENT DOCUMENTS

| 4,777,677 A | 10/1988 | Dugan |
| 4,911,995 A | 3/1990 | Belanger et al. |

(Continued)

FOREIGN PATENT DOCUMENTS

| EP | 2234188 A1 | 9/2010 |
| JP | 2001511409 A | 8/2001 |

(Continued)

OTHER PUBLICATIONS

"U.S. Appl. No. 12/980,993, Response filed Aug. 15, 2013 to Non Final Office Action dated May 15, 2013", 12 pgs.
(Continued)

*Primary Examiner* — Jeremiah R Smith
(74) *Attorney, Agent, or Firm* — Schwegman Lundberg & Woessner, P.A.

(57) ABSTRACT

An implantable device, such as a pacer, defibrillator, or other cardiac rhythm management device, can include one or more MRI Safe components. In an example, the implantable device includes a battery including a first electrode and a second electrode separate from the first electrode. The second electrode includes a first surface and a second surface. The second electrode includes a slot through the second electrode from the first surface toward the second surface. The slot extends from a perimeter of the second electrode to an interior of the second electrode. The slot is configured to at least partially segment a surface area of the second electrode to reduce a radial current loop size in the second electrode.

19 Claims, 8 Drawing Sheets

Related U.S. Application Data continuation of application No. 12/980,993, filed on Dec. 29, 2010, now Pat. No. 8,841,019.

(60) Provisional application No. 61/291,585, filed on Dec. 31, 2009.

(51) Int. Cl.

| | | |
|---|---|---|
| *A61N 1/375* | (2006.01) | |
| *H01M 4/06* | (2006.01) | |
| *H01M 4/40* | (2006.01) | |
| *H01M 4/70* | (2006.01) | |
| *H01M 6/14* | (2006.01) | |
| *A61N 1/08* | (2006.01) | |
| *H01M 4/86* | (2006.01) | |
| *H01M 4/36* | (2006.01) | |

(52) U.S. Cl.
CPC ............... *H01M 4/06* (2013.01); *H01M 4/40* (2013.01); *H01M 4/661* (2013.01); *H01M 4/669* (2013.01); *H01M 4/70* (2013.01); *H01M 6/14* (2013.01); *H01M 4/366* (2013.01); *H01M 4/667* (2013.01); *H01M 4/8657* (2013.01); *Y10T 29/49108* (2015.01); *Y10T 29/49112* (2015.01)

(56) References Cited

U.S. PATENT DOCUMENTS

| | | | |
|---|---|---|---|
| 5,028,500 | A | 7/1991 | Fong et al. |
| 6,067,474 | A | 5/2000 | Schulman et al. |
| 6,185,452 | B1 | 2/2001 | Schulman et al. |
| 6,562,494 | B1 | 5/2003 | Tsai et al. |
| 7,765,005 | B2 | 7/2010 | Stevenson et al. |
| 7,769,457 | B2 | 8/2010 | Fonte |
| 8,841,019 | B2 | 9/2014 | Lyden et al. |
| 2003/0129469 | A1 | 7/2003 | Sun et al. |
| 2007/0202401 | A1 | 8/2007 | Viavattine |
| 2009/0096413 | A1 | 4/2009 | Partovi et al. |
| 2010/0104910 | A1* | 4/2010 | Devoe ................. H01M 8/0215 429/414 |
| 2011/0159371 | A1 | 6/2011 | Lyden et al. |
| 2014/0335422 | A1 | 11/2014 | Lyden et al. |

FOREIGN PATENT DOCUMENTS

| | | |
|---|---|---|
| JP | 2006014872 A | 1/2006 |
| JP | 2008519402 A | 6/2008 |
| WO | WO-2011082236 A1 | 7/2011 |

OTHER PUBLICATIONS

"U.S. Appl. No. 12/980,993, Examiner Interview Summary dated Aug. 12, 2013", 3 pgs.
"U.S. Appl. No. 12/980,993, Examiner Interview Summary dated Nov. 14, 2013", 3 pgs.
"U.S. Appl. No. 12/980,993, Final Office Action dated Oct. 4, 2013", 18 pgs.
"U.S. Appl. No. 12/980,993, Non Final Office Action dated May 15, 2013", 17 pgs.
"U.S. Appl. No. 12/980,993, Notice of Allowance dated Mar. 18, 2014", 13 pgs.
"U.S. Appl. No. 12/980,993, Response filed Dec. 4, 2013 to Final Office Action dated Oct. 4, 2013", 13 pgs.
"U.S. Appl. No. 14/445,864, Advisory Action dated Nov. 4, 2016", 3 pgs.
"U.S. Appl. No. 14/445,864, Examiner Interview Summary dated Aug. 15, 2018", 3 pgs.
"U.S. Appl. No. 14/445,864, Final Office Action dated Jun. 8, 2018", 7 pgs.
"U.S. Appl. No. 14/445,864, Final Office Action dated Jul. 10, 2017", 14 pgs.
"U.S. Appl. No. 14/445,864, Final Office Action dated Aug. 26, 2016", 15 pgs.
"U.S. Appl. No. 14/445,864, Non Final Office Action dated Jan. 13, 2017", 14 pgs.
"U.S. Appl. No. 14/445,864, Non Final Office Action dated Apr. 7, 2016", 13 pgs.
"U.S. Appl. No. 14/445,864, Non Final Office Action dated Nov. 30, 2017", 13 pgs.
"U.S. Appl. No. 14/445,864, Notice of Allowance dated Oct. 11, 2018", 9 pgs.
"U.S. Appl. No. 14/445,864, Preliminary Amendment filed Aug. 25, 2014", 6 pgs.
"U.S. Appl. No. 14/445,864, Response filed Feb. 28, 2018 to Non Final Office Action dated Nov. 30, 2017", 10 pgs.
"U.S. Appl. No. 14/445,864, Response filed Apr. 12, 2017 to Non Final Office Action dated Jan. 13, 2017", 11 pgs.
"U.S. Appl. No. 14/445,864, Response filed Sep. 10, 2018 to Final Office Action dated Jun. 8, 2018", 9 pgs.
"U.S. Appl. No. 14/445,864, Response filed Oct. 10, 2017 to Final Office Action dated Jul. 10, 2017", 10 pgs.
"U.S. Appl. No. 14/445,864, Response filed Oct. 26, 2016 to Final Office Action dated Aug. 26, 2016", 13 pgs.
"European Application Serial No. 10801081.0, Examination Notification Art 94(3) dated Apr. 21, 2015", 4 pgs.
"International Application Serial No. PCT/US2010/062368, International Preliminary Report on Patentability dated Jul. 12, 2012", 7 pgs.
"International Application Serial No. PCT/US2010/062368, Search Report dated Mar. 4, 2011", 4 pgs.
"International Application Serial No. PCT/US2010/062368, Written Opinion dated Mar. 4, 2011", 7 pgs.
"Japanese Application Serial No. 2012-547266, Office Action dated Apr. 22, 2014", With English Translation, 12 pgs.
"Japanese Application Serial No. 2012-547266, Office Action dated Aug. 20, 2013", With English Translation, 5 pgs.

* cited by examiner

US 10,682,522 B2

1

IMPLANTABLE MEDICAL DEVICE INCLUDING EDDY CURRENT REDUCING BATTERY

CLAIM OR PRIORITY

This application is a continuation of U.S. application Ser. No. 14/445,864, filed Jul. 29, 2014, which is a continuation of U.S. application Ser. No. 12/980,993, filed Dec. 29, 2010, now issued as U.S. Pat. No. 8,841,019, which claims the benefit of U.S. Provisional Application No. 61/291,585, filed on Dec. 31, 2009, under 35 U.S.C. § 119(e), each of which is incorporated herein by reference in its entirety.

BACKGROUND

Implantable medical devices (IMDs) can perform a variety of diagnostic or therapeutic functions. For example, an IMD can include one or more cardiac function management features, such as to monitor the heart or to provide electrical stimulation to a heart or to the nervous system, such as to diagnose or treat a subject, such as one or more electrical or mechanical abnormalities of the heart. Examples of IMDs can include pacers, automatic implantable cardioverter-defibrillators (ICDs), or cardiac resynchronization therapy (CRT) devices, among others. Nuclear magnetic resonance imaging (MRI), is a medical imaging technique that can be used to visualize internal structure of the body. MRI is an increasingly common diagnostic tool, but can pose risks to a person with an IMD, such as a patient undergoing an MRI scan or a person nearby MRI equipment, or to people having a conductive implant.

In a MR field, an item, such as an IMD, can be referred to as "MR Safe" if the item poses no known hazard in all MRI environments. In an example, MR Safe items can include non-conducting, non-metallic, non-magnetic materials, such as glass, porcelain, a non-conductive polymer, etc. An item can be referred to as "MR Conditional" in the MR field if the item has been demonstrated to pose no known hazards in a specified MRI environment with specified conditions of use (e.g., static magnetic field strength, spatial gradient, time-varying magnetic fields, RF fields, etc.). In certain examples, MR Conditional items can be labeled with testing results sufficient to characterize item behavior in a specified MRI environment. Testing can include, among other things, magnetically induced displacement or torque, heating, induced current or voltage, or one or more other factors. An item known to pose hazards in all MRI environments, such as a ferromagnetic scissors, can be referred to as "MR Unsafe."

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

2

Figure 3A:
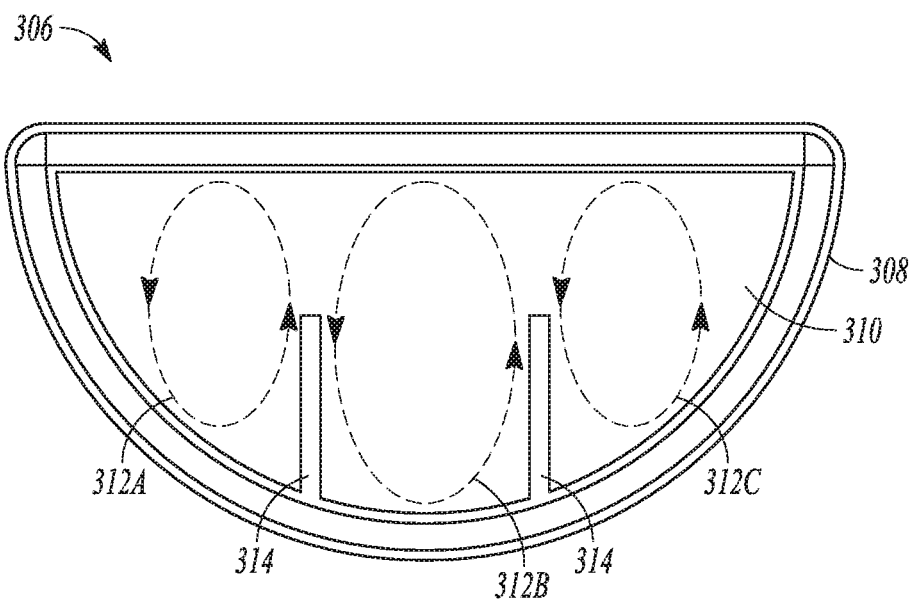
FIG. 3A illustrates a cut-away view of an example of a battery including a segmented electrode.
Figure 3B:
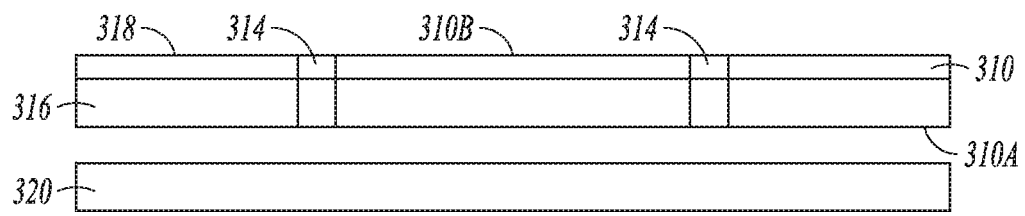

FIG. 3B illustrates a side view of two example electrodes of the battery of FIG. 3A.

Figure 3C:
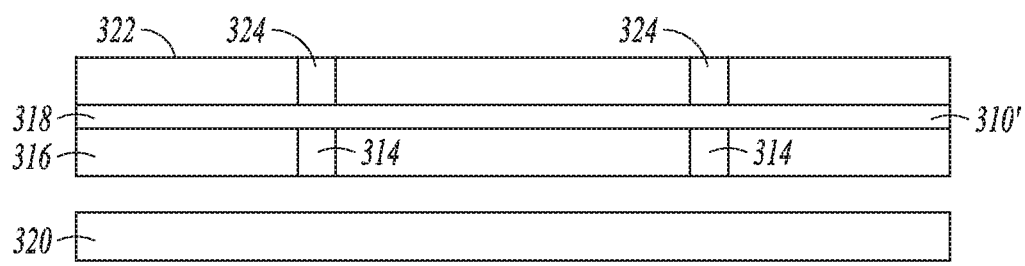

FIG. 3C illustrates a side view of two example electrodes of the battery of FIG. 3A.

FIGS. 4-10 illustrate examples of segmented electrodes.

Figure 11:
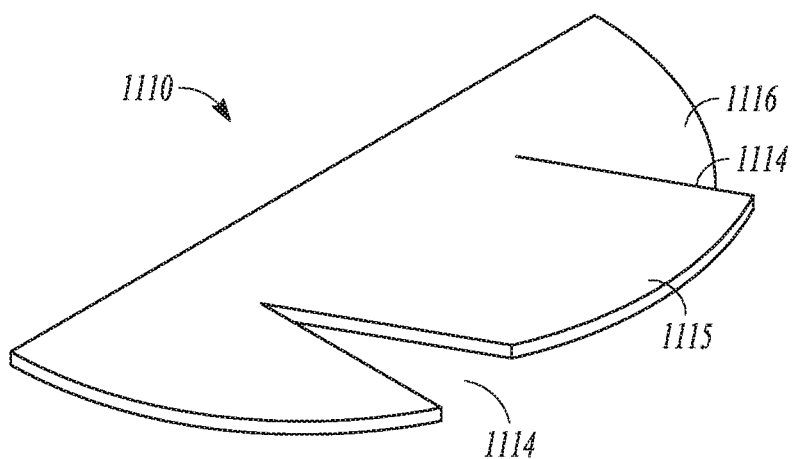

FIG. 11 illustrates a perspective view of an example of a segmented electrode.

Figure 12:
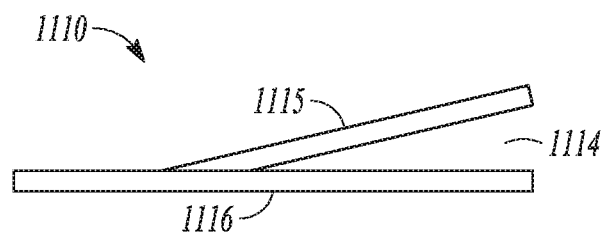

FIG. 12 illustrates a side view of the segmented electrode of FIG. 11.

Figure 13:
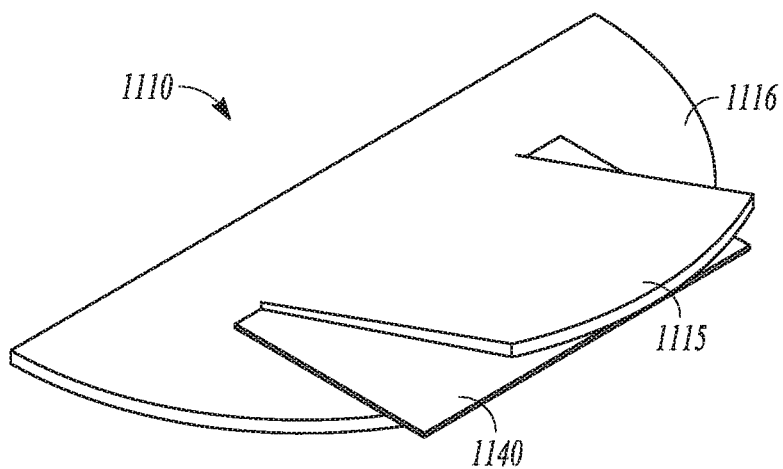

FIG. 13 illustrates a perspective view of the segmented electrode of FIG. 11 including insulating material within slots of the segmented electrode.

Figure 14:
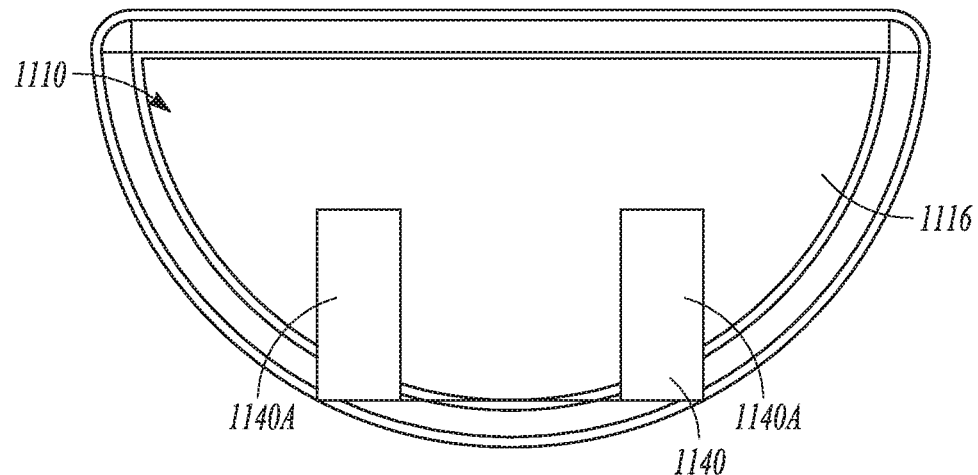

FIG. 14 illustrates a cut-away view of an example of a battery including a segmented electrode including insulating material.

Figure 15:
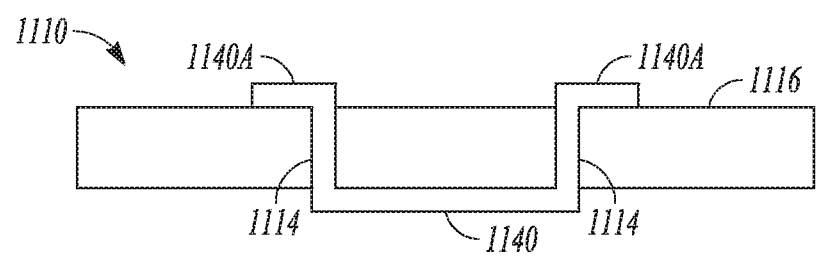

FIG. 15 illustrates a side view of the segmented electrode of FIG. 14.

Figure 16:
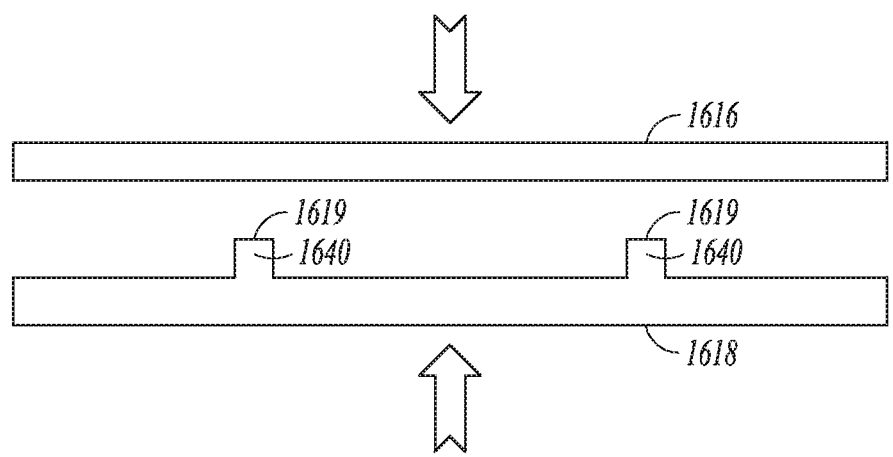

FIG. 16 illustrates a side view of an example of an electrode prior to pressing layers of the electrode together.

Figure 17:
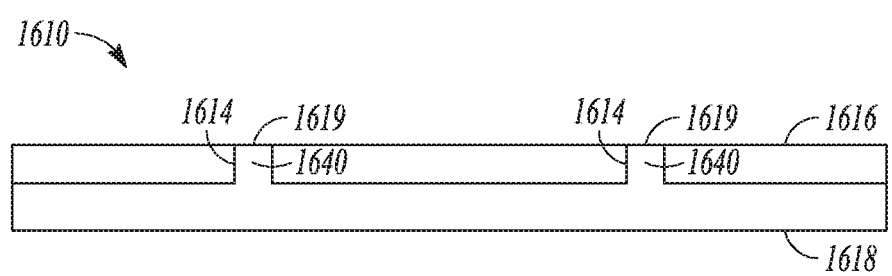

FIG. 17 illustrates a side view of the electrode of FIG. 16 after pressing together of the layers of the electrode.

Figure 18:
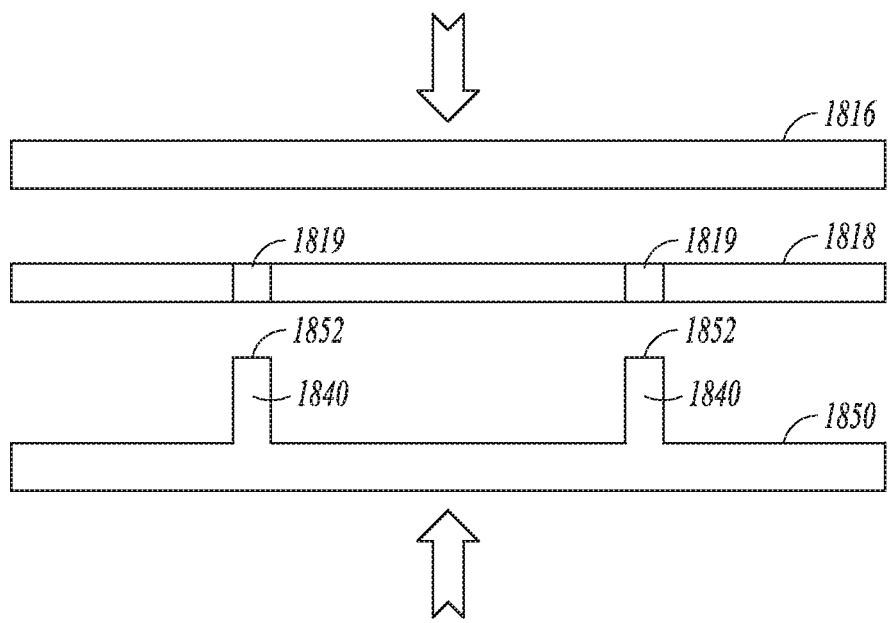

FIG. 18 illustrates a side view of an example of an electrode prior to pressing layers of the electrode together.

Figure 19:
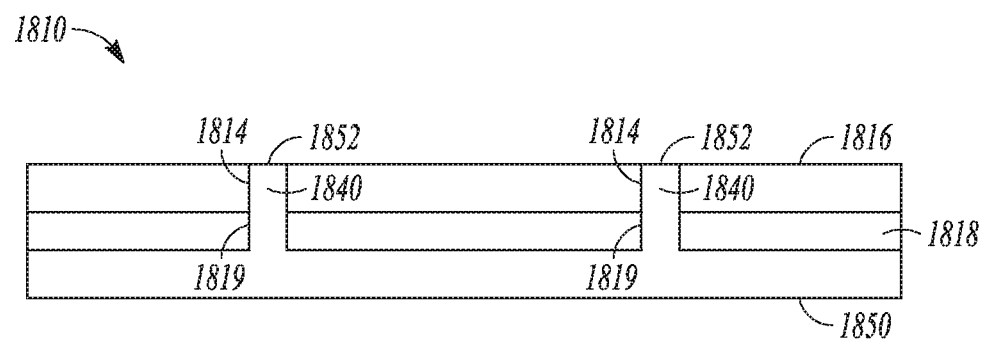

FIG. 19 illustrates a side view of the electrode of FIG. 18 after pressing together of the layers of the electrode.

Figure 20:
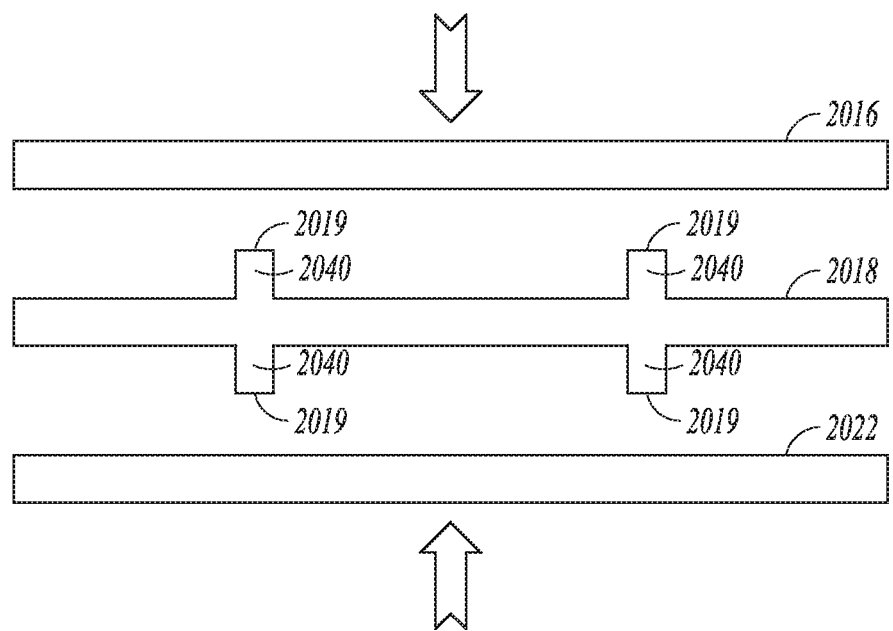

FIG. 20 illustrates a side view of an example of an electrode prior to pressing layers of the electrode together.

Figure 21:
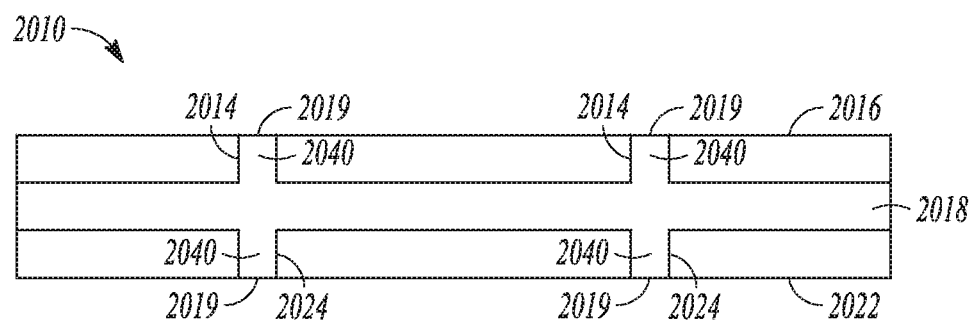

FIG. 21 illustrates a side view of the electrode of FIG. 20 after pressing together of the layers of the electrode.

DETAILED DESCRIPTION

Nuclear magnetic resonance (NMR) devices (e.g., an MRI scanner, an NMR spectrometer, or other NMR device) can produce both static and time-varying magnetic fields. For example, an MRI scanner can provide a strong static magnetic field, $B_0$, such as to align nuclei within a subject to the axis of the $B_0$ field. The $B_0$ can provide a slight net magnetization (e.g., a "spin polarization") among the nuclei in bulk because the spin states of the nuclei are not randomly distributed among the possible spin states. Because the resolution attainable by NMR devices can be related to the magnitude of the $B_0$ field, a stronger $B_0$ field can be used to spin polarize the subject's nuclei to obtain finer resolution images. NMR devices can be classified according the magnitude of the $B_0$ field used during imaging, such as a 1.5 Tesla $B_0$ field, a 3.0 Tesla $B_0$ field, etc.

After nuclei are aligned using the $B_0$ field, one or more radio frequency (RF) magnetic excitation pulses can be delivered such as to alter the alignment of specified nuclei (e.g., within a particular volume or plane to be imaged within the subject). The power, phase, and range of frequencies of the one or more RF excitation pulses can be selected, such as depending on the magnitude of the $B_0$ field, the type or resonant frequency of the nuclei to be imaged, or one or more other factors. After the RF excitation pulses are turned off, one or more RF receivers can be used to detect a time-varying magnetic field (e.g., a flux) developed by the nuclei as they relax back to a lower energy state, such as the spin polarized state induced by the static magnetic field, $B_0$.

One or more gradient magnetic fields can also be provided during MR, such as to create a slight position-dependent variation in the static polarization field. The variation in the static polarization field slightly alters the resonant frequency of the relaxing nuclei, such as during relaxation after excitation by the one or more RF pulses. Using the gradient field along with the static field can provide "spatial localization"

of signals detected by the RF receiver, such as by using frequency discrimination. Using a gradient field allows a volume or plane to be imaged more efficiently. In a gradient field example, signals received from relaxing nuclei can include energy in respective unique frequency ranges corresponding to the respective locations of the nuclei.

Active MRI equipment can induce unwanted torques, forces, or heating in an IMD or other conductive implant, or can interfere with operation of the IMD. In certain examples, the interference can include disruption in sensing by the IMD, interference in communication between the IMD and other implants or external modules during MRI operation, or disruption in monitoring or therapeutic function of the IMD.

During an MRI scan, the one or more RF excitation pulses can include energy delivered at frequencies from less than 10 MHz to more than 100 MHz, such as corresponding to the nuclear magnetic resonances of the subject nuclei to be imaged. The gradient magnetic field can include energy delivered at frequencies lower than the RF excitation pulses, because most of the AC energy included in the gradient field is provided when the gradient field is ramping or "slewing." The one or more gradient magnetic fields can be provided in multiple axes, such as including individual time-varying gradient fields provided in each of the axes to provide imaging in multiple dimensions.

In an example, the static field, $B_0$, can induce unwanted forces or torques on ferromagnetic materials, such as steel or nickel. The forces or torques can occur even when the materials are not directly within the "bore" of the MRI equipment—because significant fields can exist near the MRI equipment. Moreover, if an electric current is switched on or off in the presence of the $B_0$ field, a significant torque or force can be suddenly imposed in the plane of the circulation of the current, even though the $B_0$ field itself is static. The induced force or torque can be minimal for small currents, but the torque can be significant for larger currents, such as those delivered during defibrillation shock therapy. For example, assuming the circulating current is circulating in a plane normal (e.g., perpendicular) to the static field, the torque can be proportional to the magnitude of the $B_0$ field, multiplied by the surface area of the current loop, multiplied by the current.

Time-varying fields, such as the gradient field or the field associated with the RF excitation pulse, can present different risks than the static field, $B_0$. For example, the behavior of a wire loop in the presence of a time-varying magnetic field can be described using Faraday's law, which can be represented by $$\varepsilon = -\frac{d\Phi_{B_1}}{dt},$$

in which $\varepsilon$ can represent the electromotive force (e.g., in volts), such as developed by a time-varying magnetic flux. The magnetic flux can be represented as $$\Phi_{B1} = \iint_S B_1 \cdot dS.$$

in which $B_1$ can represent an instantaneous magnetic flux density vector (e.g., in Webers per square meter, or Tesla). If $B_1$ is relatively uniform over the surface S, then the magnetic flux can be approximately $\Phi_{B1} = |B_1||A|$, where A can represent the area of the surface S. Operating MRI equipment can produce a time-varying gradient field having a slew rates in excess of 100 Tesla per second (T/s). The slew rate can be similar to a "slope" of the gradient field, and is thus similar to $$\frac{d\Phi_{B_1}}{dt}.$$

The electromotive force (EMF) of Faraday's law can cause an unwanted heating effect in a conductor—regardless of whether the conductor is ferromagnetic. EMF can induce current flow in a conductor (e.g., a housing of an IMD, one or more other conductive regions within an IMD, or one or more other conductive implants). The induced current can dissipate energy and can oppose the direction of the change of the externally applied field (e.g., given by Lenz's law). The induced current tends to curl away from its initial direction, forming an "eddy current" over the surface of the conductor, such as due to Lorentz forces acting upon electrons moving through the conductor. Because non-ideal conductors have a finite resistivity, the flow of induced current through the conductor can generate heat. The induced heat can cause a significant temperature rise in or near the conductor over the duration of the scan. The eddy current power deposition can be proportional to the square of both the peak flux density and the frequency of the excitation. If significant heating occurs, it can cause tissue damage or death.

As described above, the MRI time varying gradient fields can induce eddy currents and heat within conductive components of the IMD. Additionally, these eddy currents can generate a magnetic moment producing a torque in the direction that aligns the eddy current magnetic moment with the MRI $B_0$ field. This torque can produce differential forces (and, in turn, vibration) between the internal components of the IMD and/or its enclosure. The resulting vibration of internal components can cause cyclical fatigue failures, for example between the battery terminal and its electrical connection to electronic subassemblies, such as a microelectronic hybrid circuit board, which can render the IMD inoperable and require premature surgical replacement. In light of this, the present inventors have recognized that induced heat and vibration can present hazards to the patient having an IMD and being subjected to an MRI environment.

Generally, induced currents, such as induced by the RF magnetic excitation pulse, can concentrate near the surface of a conductor, a phenomenon that can be referred to as the skin effect. The skin effect can limit both the magnitude and depth of the induced current, thus reducing power dissipation. However, the gradient field can include energy at a much lower frequency than the RF magnetic excitation field, which can more easily penetrate through the housing of the IMD. Unlike the field from the RF excitation pulse, the gradient field can more easily induce bulk eddy currents in one or more conductors within the IMD housing, such as within one or more circuits, capacitors, batteries, or other conductors.

Aside from heating, the MRI gradient induced EMF can create, among other things, non-physiologic voltages that can cause erroneous sensing of cardiac electrical activity, or the EMF can create a voltage sufficient to depolarize cardiac tissue or render the cardiac tissue refractory, possibly affecting pacing therapy. In an illustrative example, an IMD can be connected to one or more leads, such as one or more subcutaneous or intravascular leads positioned to monitor the patient, or to provide one or more therapies to the patient. In this illustrative example, a surface area of a "circuit" including the lead, the housing of the IMD, and a path through at least partially conductive body tissue between an electrode on the lead and the IMD housing can be more than 300 square centimeters, or more than 0.03 square meters. Thus, using Faraday's law, the electromotive force (EMF) developed through the body tissue between the electrode (e.g., a distal tip or ring electrode) of the lead and the housing of the IMD can be more than 0.03 square meters times 100 t/s, or more than 3 volts.

The present inventors have recognized, among other things, that it is desirable for IMDs to include increased safety within an MRI environment. For instance, the present inventors have recognized that it is desirable for IMDs to include a decreased response to the magnetic fields present within or otherwise proximate an MRI device. Such responses include, but are not limited to, heating, vibration or other induced movement, induced voltages, and the like. In some examples, the present inventors have recognized that it is desirable to reduce the magnetic field response of IMD batteries.

Figure 1:
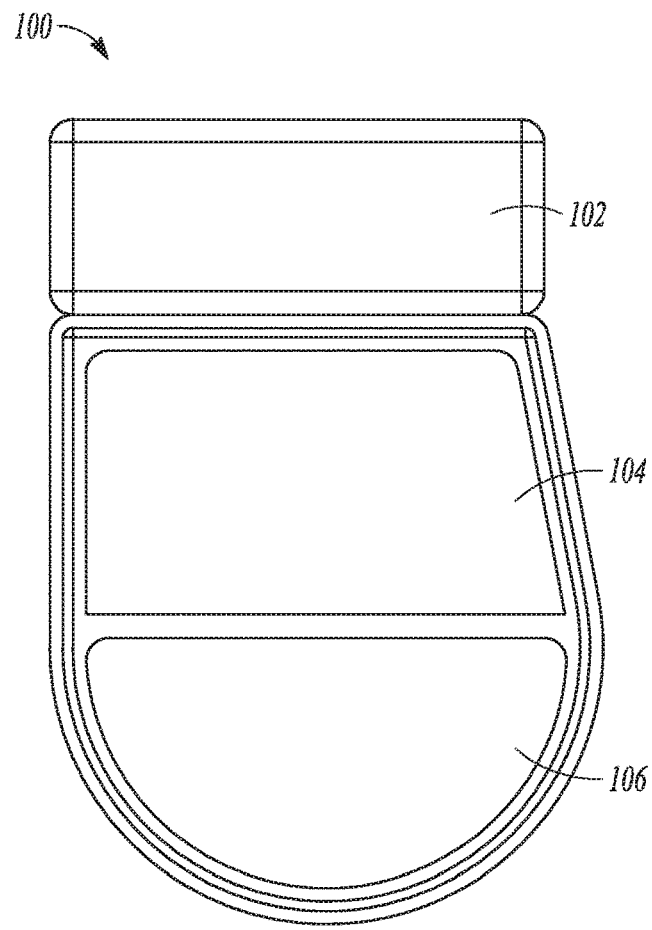
FIG. 1 illustrates a cut-away view of an IMD showing basic components of the IMD.

Referring to FIG. 1, an example of an IMD 100 is shown. The IMD 100, in an example, includes a header 102 for attaching a component such as a lead to the IMD. In an example, the IMD 100 includes an electronic module 104 including electronics of the IMD 100 associated with the operation and functioning of the IMD 100 within a patient. In some examples, the IMD 100 includes a cell or battery 106. In various examples, one of more of the components 102, 104, 106, or other components of IMDs which are not shown in FIG. 1, such as capacitors, leads, etc., can include decreased response to magnetic fields for increased safety within the MRI environment. As such, the description herein, although describing primarily decreased MR response in batteries, can be applied to any components or combinations of components of an IMD, including also metal or otherwise conductive enclosures of the components of the IMD or of the IMD itself. Examples of IMDs that can include metal enclosures and/or internal large surface area components include but are not limited to, cardiac pacemakers; automatic implantable cardioverter-defibrillators (ICDs); cardiac resynchronization therapy and defibrillator (CRT-D) devices; neuromodulators including deep brain stimulators (DBS), various pain control devices, and lead systems for stimulation of the spinal cord, muscles, and other nerves of the body (such as, for instance, the vagal nerve); implantable diagnostic devices for monitoring cardiac function; cochlear implants; and drug pumps for administering periodic or demand based pharmacological therapy. In general, it is contemplated that the present description can relate to or be applied to any IMDs that have metallic enclosures and/or include relatively large surface area internal conductive components, which can circulate eddy currents in response to the MRI time varying gradient magnetic fields to cause heat and/or vibration in the IMD.

Figure 2:
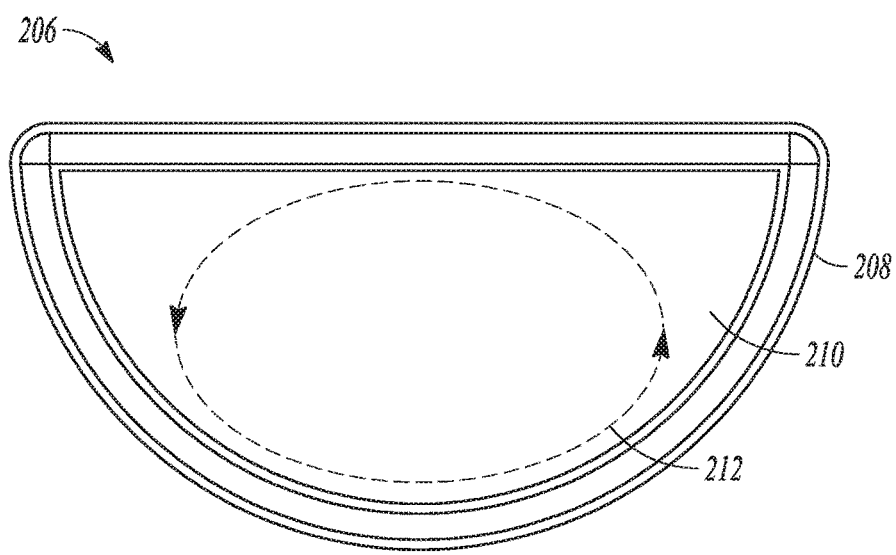
FIG. 2 illustrates a cut-away view of a battery including an un-segmented electrode.

Referring to FIG. 2, a battery 206 for an IMD includes a housing 208 that is partially cut away to show an electrode 210 of the battery 206. An arrow 212 is depicted on the electrode 210 to portray an example radial current or eddy current of the electrode 210, such as could be induced by a gradient field of an MRI device. In an example, an induced eddy current can interact with the static magnetic field and can result in vibration or other movement of the battery 206. In another example, the induced eddy current can be dissipated as heat to elevate the temperature of the battery 206. For a given time varying gradient field, the induced torque and/or generated heat are functions of the material and the geometry of the electrode 210. For instance, the eddy current induced heating and vibration are generally proportional to the square of the surface area of the conductor, or, in the example of FIG. 2, generally the area encompassed by the induced eddy current shown by arrow 212. Because of the relatively large surface area (and the relatively large loop 212 of the eddy current) of the example electrode 210, the battery 206 can be a substantial source of heat and/or vibration when placed within an MRI environment. Accordingly, reduction of the loop size of an induced eddy current present in, for instance, an electrode of a battery of an IMD, is contemplated herein to reduce heating and/or movement induced in an IMD subjected to an MRI environment. Several examples of such electrodes are described below.

Referring to FIG. 3A, in an example, a battery 306, for use, for instance, in an IMD, includes a housing 308 that is shown partially cut away to show a segmented electrode 310 of the battery 306. In some examples, the segmented electrode 310 includes high resistance sections to segment the electrode 310. In some examples, the high resistance sections are formed by at least partially cutting through the electrode 310. In further examples, the segmented electrode 310 includes one or more openings or slots 314. In an example, the segmented electrode 310 includes two openings or slots 314 extending from a perimeter of the electrode 310 to an interior portion of the electrode 310. In further examples, more or less than two slots can be formed in the electrode. In still further examples, the one or more slots can be formed in different areas of the electrode. In the example shown in FIG. 3A, the slots 314 provide breaks in the surface area of the electrode 310, which can result in smaller radial current loops of eddy currents (relative to the loop size of the eddy current of an unsegmented electrode, such as the example electrode 210 of FIG. 2), as depicted by arrows 312A, 312B, 312C. By reducing the loop size of the eddy currents in the electrode 310, in an example, the heating and/or movement induced by an MRI environment can be reduced to a level at which the IMD and/or the battery 306 of the IMD are deemed MRI Safe. Because removal of electrode material can generally adversely affect performance and effectiveness (longevity, for instance) of the battery 306, a consideration in segmentation of the electrode 310 is minimal material removal. In an example, by optimizing a pattern of the segmentation of the electrode 310, the performance of the battery 306 can be minimally impacted while, at the same time, sufficiently minimizing eddy current loop size to result in an MRI Safe battery 306.

Referring now to FIGS. 3A and 3B, in an example, the battery 306 includes a first electrode 320. A second electrode (such as, the segmented electrode 310) is separate from the first electrode 320. In an example, the second electrode 310 includes a first surface 310A facing the first electrode 320 and an oppositely disposed second surface 310B facing away from the first electrode 320. In an example, the first and second electrodes are separated by a relatively small distance. In a further example, the first and second electrodes 320, 310 are separated by a battery separator, such as, for instance, a separator membrane. In an example, the first and second electrodes 320, 310 include substantially similar footprints. The second electrode 310, in an example, includes one or more slots 314, which extend through the second electrode 310 from the first surface 310A toward the second surface 310B. In an example, the one or more slots 314 extend completely through the second electrode 310 from the first surface 310A to the second surface 310B. The one or more slots 314, in an example, extend from a perimeter of the second electrode 310 to an interior of the second electrode 310. The one or more slots 314 can be configured to at least partially segment a surface area of the second electrode 310 to reduce a radial current loop size (as depicted by arrows 312A, 312B, 312C) in the second electrode 310. In some examples, depending on the conductivity, thickness, and number of first electrodes 320, it can be desirable to segment the first electrode 320 to reduce the overall heating of the battery to level that results in a MR conditionally safe design. In other examples, depending upon the constitutive materials and geometric form of the one or more first electrodes 320, it can be desirable to segment in the one or more first electrodes 320.

In an example, the first electrode 320 includes a cathode and the second electrode 310 includes an anode. In further examples, although shown in FIG. 3B with one first electrode 320 and one second electrode 210, the battery 306 can include more than one first electrode 320 and/or more than one second electrode 310, depending upon the power requirements of the IMD or other device within which the battery 306 is to be used. In an example, the first electrode 320 can be substantially planar. In another example, the second electrode 310 can be substantially planar. In other examples, the first and second electrodes 320, 310 can be non-planar.

Referring to FIG. 3B, in an example, the second electrode 310 includes a first layer 316 forming the first surface 310A of the second electrode 310 and a second layer 318 abutting the first layer 316, the second layer 318 forming the second surface 310B of the second electrode 310. In an example, the first layer 316 includes lithium. In some examples, the second layer 318 can include a conductive material. In an example, the second layer 318 can include nickel. In a further example, the second layer 318 includes stainless steel. In this example, due to the malleability of lithium, a relatively stiff second layer 318 is desirable in order to maintain the lithium first layer 316 in the desired shape. Moreover, a non-ferromagnetic material is also desirable to further decrease magnetic response to the MRI environment. For at least these reasons, the stainless steel second layer 318 is contemplated for use in the second electrode 310. However, it is further contemplated in other examples that other materials can be used for the second layer 318 provided that the materials provide a stiff backing member for the lithium first layer 316 while, at the same time, providing a decreased response to magnetic fields present in the MRI environment.

In an example, the second layer 318 can be a mesh-like backing member to allow for increased engagement between the first and second layers 316, 318. That is, in an example, when the lithium first layer 316 is pressed against the second layer 318, the malleable lithium deforms within voids of the mesh-like second layer 318 to engage the first and second layers 316, 318. In other examples, second layers 318 including other patterns can be used for engagement of the first and second layers 316, 318. In still another example, the second layer 318 can be a flat sheet and an adhesive or other bonding compound can be used to engage the first and second layers 316, 318 of the second electrode.

In an example, the one or more slots 314 extend through at least the first layer. In an example in which the first layer 316 includes lithium, it is desirable for the one or more slots 314 to extend through the lithium first layer 316 to decrease magnetic response of the second electrode 310. Because of the high conductivity of lithium, the lithium first layer 316 can be particularly susceptible to induced heat and movement within an MRI environment.

For at least this reason, it is desirable to segment the lithium first layer 316 of the second electrode 310. In an example in which the second layer 318 includes stainless steel, the second layer 318 need not be segmented due to decreased response of stainless steel within the MRI environment. However, in another example, the one or more slots 314 can extend through the second layer 318 as well as the first layer 316. In an example, both the first and second layers 316, 318 can be segmented for ease of manufacture of the second electrode 310. For instance, when die pressing is used to segment the second electrode 310, both of the first and second layers 316, 318 can be segmented after the first and second layers 316, 318 are engaged. In another example, the second layer 318 can remain un-segmented by segmenting the first layer 316 using die pressing prior to engagement of the first and second layers 316, 318 and then engaging the segmented first layer 316 to the un-segmented second layer 318.

In various examples, the battery 306 can include a second electrode differently configured from the second electrode 310 described above. The configuration of the second electrode can depend on various factors including performance requirements of the battery 306, type of device being powered by the battery 306, or the like. Referring to FIG. 3C, in an example, the battery 306 can include a segmented second electrode 310' that is substantially similar to the second electrode 310 described above, but further includes a third layer 322 abutting the second layer 318 along a surface of the second layer 318 facing away from the first layer 316, such that the second layer 318 is disposed between the first and third layers 316, 322. In an example, the third layer 322 includes a similar material to the material of the first layer 316. In a further example, both the first and third layers 316, 322 include lithium. In another example, the third layer 322 can include a material different than the material of the first layer 316. In an example, the third layer 322 can be segmented. For instance, in an example, the second electrode 310' can include one or more slots 324 extending through the third layer 322. In one example, the slots 324 of the third layer 322 are aligned with the one or more slots 314 of the first layer 316. In another example, the slots 324 of the third layer 322 are offset from or otherwise out of alignment with the one or more slots 314 of the first layer 316.

Referring now to FIGS. 4-10, various examples of segmented second electrodes can include variously configured high resistance sections or segmentations to break up surface areas of the second electrodes to reduce the size of radial current loops and reduce the response of the second electrodes within the MRI environment.

Figure 4:
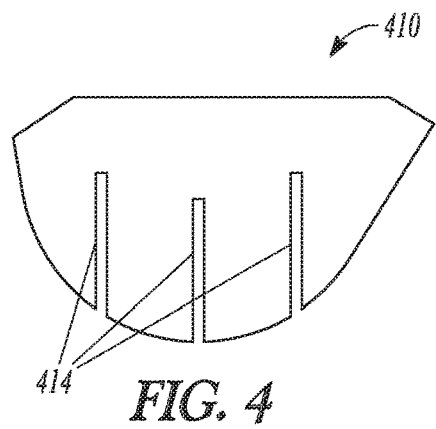
Figure 5:
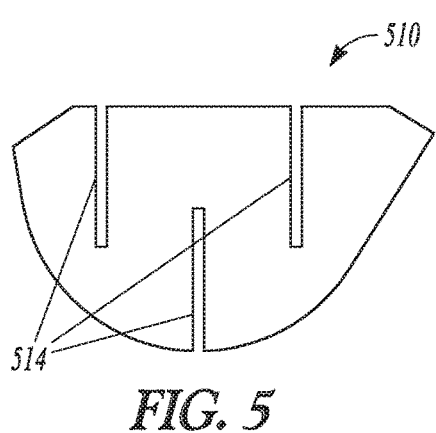
Figure 6:
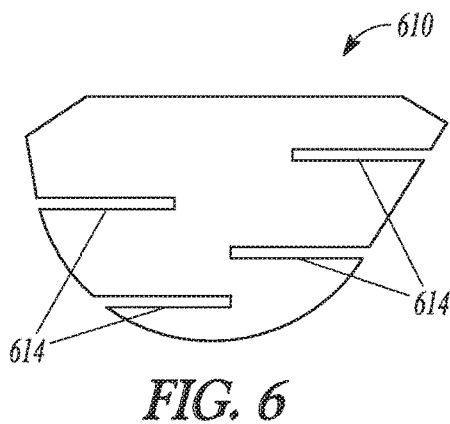

For instance, with respect to FIGS. 4-6, segmented second electrodes 410, 510, 610 can include variously configured slots 414, 514, 614, although it is contemplated that other slot or opening configurations can be used other than those shown herein, provided the slots or openings provide segmentation and decreased response of the second electrodes within the MRI environment.

Figure 7:
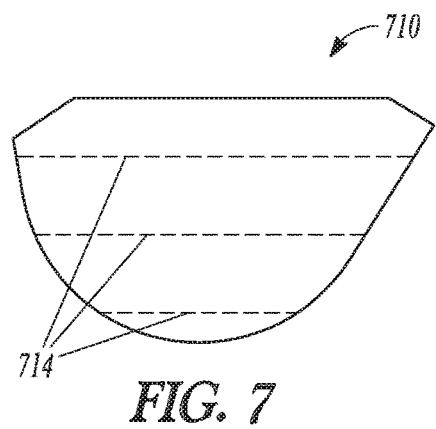
Figure 8:
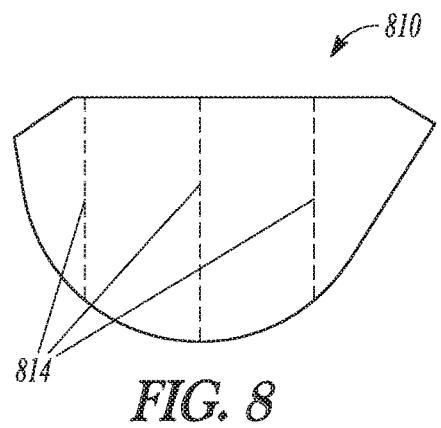
Figure 9:
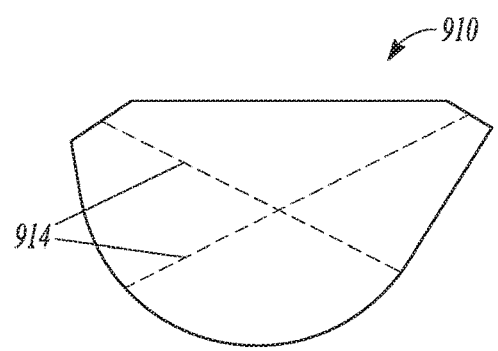

Referring to FIGS. 7-9, in further examples, segmented second electrodes 710, 810, 910 can include thinning of the second electrodes 710, 810, 910 along lines 714, 814, 914 to break up surface areas of the second electrodes 710, 810, 910. Such thinning of the second electrodes 710, 810, 910 can be accomplished by, for instance, scoring, embossing, or cutting the second electrodes 710, 810, 910 along the lines 714, 814, 914.

Figure 10:
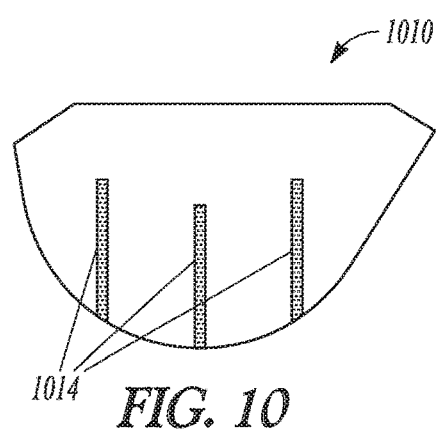

Referring to FIG. 10, in another example, a segmented electrode 1010 includes one or more high resistance sections 1014. In various examples, the high resistance sections 1014 can be created in various ways. In some examples, the one or more high resistance sections 1014 can be created by oxidation or other chemical reactions. In some examples, masking can be used to control oxidation or other chemical reactions used in creating the one or more high resistive sections 1014.

In an example, a positive photo resistive coating can be applied to the electrode 1010. A mask can then be applied to the electrode 1010 and a light source, such as, for instance, an ultraviolet light source, can be applied to decompose the photo resistive coating that is exposed through the mask. The electrode 1014 can then be subjected to an oxidation chamber, such as, for instance, an oxygen plasma chamber, to etch away the electrode that is not covered by photo resistive material. Depending on the exposure time in the oxidation chamber, the exposed portion will be oxidized, creating the one or more high resistance sections 1014 that provide a higher resistance pathway than the remainder of the segmented electrode 1010 and, in turn, provide segmentation and decreased response of the segmented electrode 1010 within the MRI environment.

In another example, the segmented electrode 1010 includes insulation or another relatively high resistance material embedded in the segmented electrode 1010 to form one or more high resistance sections 1014. In still another example, the segmented electrode 1010 includes insulation or another relatively high resistance material constructed into the segmented electrode 1010 to form one or more high resistance sections 1014. In these examples, the one or more high resistance sections 1014 provide segmentation and decreased response of the segmented electrode 1010 within the MRI environment. That is, the one or more high resistance sections 1014 can break the path of induced eddy currents by the gradient field of the MRI environment, thereby decreasing battery heating and/or vibration.

Referring to FIGS. 11-15, in some examples, a second electrode 1110 includes an insulating or separating material 1140 within one or more high resistance sections. In some examples, the one or more high resistance sections include one or more openings or slots 1114 in the second electrode 1110. The separating material 1140 can be included within the one or more slots 1114, for instance, to inhibit dendritic growth across the one or more slots 1114 or to aid in manufacturing ease while removing a relatively small or minimal amount of electrode material. Dendritic growth of the second electrode 1110 can result in renewed connection of portions of the second electrode 1110 across the one or more slots 1114, which can result in larger radial current loops in the second electrode 1114 and reduce the effectiveness of the segmentation of the second electrode 1114. That is, dendritic growth across the one or more slots 1114 can allow a conductive connection of the portions of the second electrode 1110 previously separated by the one or more slots 1114 to allow relatively large radial current loops in the second electrode 1110, resulting in increased response of the second electrode 1110 to an MRI environment. Depending on the amount of dendritic growth, segmentation of the second electrode 1110 can become ineffective and result in an MRI Unsafe electrode. In an example, by inserting an insulative material in slots 1114, separated surface areas can be created to reduce current loop radius while still maintaining a relatively high amount of material in the electrode. In various examples, the separating material 1140 can be configured to maintain separation of the second electrode 1114 along a length of the one or more slots 1114 and inhibit the possibility of dendritic growth across the one or more slots 1114 of the second electrode 1110.

In an example, a first layer 1116 of the second electrode 1110 can be sheared to create a tab 1115 raised from a plane of the first layer 1116, as seen in FIGS. 11 and 12. Shearing of the first layer 1116 can be accomplished, in an example, using a die pressing operation. Shearing of the first layer 1116 can create the slots 1114 in the first layer 1116 of the second electrode 1110. Once the tab 1115 is raised, the separating material 1140 can be positioned between the raised tab 1115 and the remainder of the second electrode 1110, as seen in FIG. 13. With the separating material 1140 in place, the raised tab 1115 can then be pressed back down in plane with the remainder of the first layer 1116 to capture portions of the insulating material 1140 within the slots 1114 to provide separation of the first layer 1116 along a length of each of the slots 1114, as shown in FIGS. 14 and 15. In various examples, a backing member or other second layer, such as those described above, can then be engaged with the first layer 1116. In another example, the tab 1115 can be flattened and the first layer can be engaged with the second layer in the same pressing operation. By segmenting the second electrode 1110 in this way, little or no material of the first layer 1116 is lost, which can limit any reductions in effectiveness or performance of the second electrode 1110 resulting from segmentation of the second electrode 1110. In some examples, portions 1140A of the separating material 1140 overlapping the first layer 1116 can mask the first layer 1116, which can result in decreased performance or effectiveness of the second electrode 1110. In an example, by keeping the amount of overlap of the portions 1140A to a minimum, reductions in performance or effectiveness of the second electrode 1110 can be kept to a minimum.

Referring to FIGS. 16 and 17, in another example, a second electrode 1610 includes one or more high resistance sections including an insulating or separating material 1640 within one or more openings or slots 1614 in the second electrode 1610 to inhibit material growth across the one or more slots 1614. In this example, the second electrode 1610 includes a backing member or second layer 1618 abutting a first layer 1616. In an example, the second layer 1618 includes one or more tabs 1619 extending from a surface of the second layer 1618. In an example, the second layer 1618 and/or the one or more tabs 1619 of the second layer 1618 provide the insulating or separating material 1640 of the second electrode 1610. In a further example, the first layer 1616 includes lithium. In some examples, the second layer 1618 can include a conductive material. In a further example, the second layer 1618 can include stainless steel. In a still further example, the second layer 1618 can include nickel. In another example, the first layer 1616 can be positioned in correspondence with the second layer 1618 in a substantially stacked manner, as shown in FIG. 16. In another example, the second layer 1618 can include nickel. The first and second layers 1616, 1618 can then be pressed together in the direction of the arrows shown in FIG. 16. During the pressing operation, the one or more tabs 1619 can be pushed through the first layer 1610, thereby forming one or more slots 1614 (the number and location of the one or more slots 1614 corresponding to the number and location of the one or more tabs 1619 of the second layer 1618) in the first layer 1616 and, at the same time, filling the one or more slots 1614 with the separating material 1640, as shown in FIG. 17, to inhibit material growth across the one or more slots 1614. In an example, the second layer 1618 and the one or more tabs 1619 of the second layer 1618 can be formed from the same material, such as, for instance, stainless steel. In another example, the one or more tabs 1619 can be formed from a material different than the material of the remainder of the second layer 1618, and the one or more tabs 1619 can be engaged to the surface of the second layer 1618 in the desired position.

Referring to FIGS. 18 and 19, in further examples, a second electrode 1810 includes one or more high resistance sections including an insulating or separating material 1840 within one or more openings or slots 1814 in the second electrode 1810 to inhibit material growth across the one or more slots 1814. In this example, the second electrode 1810 includes a backing member or second layer 1818 abutting a first layer 1816. In an example, the second layer 1818 includes one or more voids 1819 in the second layer 1818. In a further example, the second electrode 1810 can include a separation layer 1850 including the insulating or separating material 1840 of the second electrode 1810. The separation layer 1850 can include one or more tabs 1852 extending from a surface of the separation layer 1850. In a further example, the first layer 1816 includes lithium. In some examples, the second layer 1818 can include a conductive material. In a further example, the second layer 1818 can include stainless steel. In a still further example, the second layer 1818 can include nickel. In this example, the separation layer 1850 need not be formed from the same material as the second layer 1818 (for instance, stainless steel) and can be formed from any material with sufficient properties to allow pressing of the one or more tabs 1852 through the first layer 1816, as described below, and to provide sufficient separation of the segmented first layer 1816. In an example, the first layer 1816, the second layer 1818, and the separation layer 1850 can be positioned in a substantially stacked manner, as shown in FIG. 18. In an example, the one or more tabs 1852 of the separation layer 1850 are aligned with a corresponding number of voids 1819 of the second layer 1818. The first layer 1816, the second layer 1818, and the separation layer 1850 can then be pressed together in the direction of the arrows shown in FIG. 18. During the pressing operation, the one or more tabs 1852 of the separation can be directed through the one or more voids 1819 of the second layer 1818 and can be pushed through the first layer 1816, thereby forming one or more slots 1814 (the number and location of the one or more slots 1814 corresponding to the number and location of the one or more tabs 1852 of the separation layer 1850) in the first layer 1816 and, at the same time, filling the one or more slots 1814 with the separating material 1840, as shown in FIG. 19, to inhibit material growth across the one or more slots 1814. In an example, the separation layer 1850 and the one or more tabs 1852 of the separation layer 1850 can be formed from the same material, such as, for instance, a polymeric material. In other examples, the separation layer 1850 and the one or more tabs 1852 are formed from a plastic material. In another example, the one or more tabs 1852 can be formed from a material different than the material of the remainder of the separation layer 1850, and the one or more tabs 1852 can be engaged to the surface of the separation layer 1850 in the desired position.

Referring to FIGS. 20 and 21, in another example, a second electrode 2010 includes one or more high resistance sections including an insulating or separating material 2040 within one or more openings or slots 2014 in a first layer 2016 of the second electrode 2010 and within one or more openings or slots 2024 in a third layer 2022 of the second electrode 2010 to inhibit material growth across the one or more slots 2014 of the first layer 2016 and the one or more slots 2024 of the third layer 2022. In this example, the second electrode 2010 includes a backing member or second layer 2018 abutting and sandwiched between the first layer 2016 and the third layer 2022. In an example, the second layer 2018 includes one or more tabs 2019 extending from a first surface of the second layer 2018 and one or more tabs 2019 extending from a second surface of the second layer 2018. In an example, the second layer 2018 and/or the one or more tabs 2019 of the second layer 2018 provide the insulating or separating material 2040 of the second electrode 2010. In a further example, the first and third layers 2016, 2022 includes lithium. In some examples, the second layer 2018 can include a conductive material. In a further example, the second layer 2018 can include stainless steel. In a still further example, the second layer 2018 can include nickel. In a further example, the first, second, and third layers 2016, 2018, 2022 can be positioned in a substantially stacked manner, as shown in FIG. 20. The first, second, and third layers 2016, 2018, 2022 can then be pressed together in the direction of the arrows shown in FIG. 20. During the pressing operation, the one or more tabs 2019 of the first surface of the second layer 2018 can be pushed through the first layer 2010 and the one or more tabs 2019 of the second surface of the second layer 2018 can be pushed through the third layer 2022, thereby forming one or more slots 2014 (the number and location of the one or more slots 2014 corresponding to the number and location of the one or more tabs 2019 of the first surface of the second layer 2018) in the first layer 2016 and forming one or more slots 2024 (the number and location of the one or more slots 2024 corresponding to the number and location of the one or more tabs 2019 of the second surface of the second layer 2018) in the third layer 2022. At the same time, this pressing operation can fill the one or more slots 2014 of the first layer 2016 and the one or more slots 2024 of the third layer 2022 with the separating material 2040, as shown in FIG. 21, to inhibit material growth across the one or more slots 2014, 2024. In an example, the one or more tabs 2019 of the first surface of the second layer 2018 are substantially aligned with the one or more tabs 2019 of the second surface of the second layer 2018. In another example, the one or more tabs 2019 of the first surface of the second layer 2018 are offset from or otherwise not aligned with the one or more tabs 2019 of the second surface of the second layer 2018. In further examples, the number of tabs 2019 of the first surface of the second layer 2018 can be greater than or less than the number of tabs 2019 of the second surface of the second layer 2018. In an example, the second layer 2018 and the one or more tabs 2019 of each of the first and second surfaces of the second layer 2018 can be formed from the same material, such as, for instance, stainless steel. In another example, the one or more tabs 2019 of each of the first and second surfaces of the second layer 2018 can be formed from a material different than the material of the remainder of the second layer 2018, and the one or more tabs 2019 can be engaged to each of the first and second surfaces of the second layer 2018 in the desired position. In another example, it is contemplated that backing materials with voids corresponding to the tabs 2019 of the second layer 2018 can be used in a manner similar to that described above with respect to FIGS. 18 and 19.

The above described examples illustrate segmented components of an IMD and methods of making such segmented IMD components, with such segmented components including a reduced response (as compared to un-segmented components) to magnetic fields present in an MRI environment. In some examples, such segmentation can be included in IMD batteries. In further examples, electrodes, including anodes and/or cathodes, of IMD batteries can be segmented in order to make the IMD battery MRI Safe. By segmenting IMD components as described above, the present inventors have recognized that eddy currents in the IMD components can be reduced, thereby resulting in reduced heating and/or vibration of the segmented components when exposed to an MRI environment. In this way, examples of the segmented IMD components and methods, such as those described above, can be used in various IMDs to make such IMDs MRI Safe.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document, for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. An implantable medical device battery comprising:
   a first electrode; and
   a second electrode separate from the first electrode, the second electrode including:
      a first layer formed of a first material having a first continuous surface and a second continuous surface opposite the first continuous surface, the first material being a conductive material; and
      a second layer positioned on the first continuous surface of the first layer, the second layer formed of a second material different from the first material, wherein the second material is lithium, wherein the second layer includes a first portion separated from a second portion by a first high resistance section, the first high resistance section having a greater resistance compared to the first and second portions of the second layer to reduce a radial current loop size in the second electrode.

2. The implantable medical device of claim 1, wherein the first surface and the second surface of the first layer are continuous surfaces.

3. The implantable medical device of claim 1, wherein the first high resistance section, along a cross-sectional view, is defined by a first surface of the first portion, a third portion of the first surface of the first layer, and a second surface of the second portion.

4. The implantable medical device of claim 1, wherein the conductive material is selected from one of stainless steel and nickel.

5. The implantable medical device of claim 1, wherein the first high resistance section is formed by a first gap between the first and second portions of the second layer.

6. The implantable medical device of claim 5, wherein the first layer includes at least one tab extending from the first surface of the first layer, wherein the tab is positioned within the first gap between the first and second portions of the second layer.

7. The implantable medical device of claim 6, wherein the tab is formed of the first material.

8. The implantable medical device of claim 6, wherein the tab is formed of a third material different from the first material.

9. The implantable medical device of claim 6, wherein the first layer includes at least one tab extending from the second surface of the first layer.

10. The implantable medical device of claim 9, wherein the second electrode further includes:
    a third layer positioned on the second surface of the first layer, the third layer formed of the second material, wherein the third layer includes a third portion separated from a fourth portion by a second high resistance section, the second high resistance section having a greater resistance compared to the third and fourth portions of the third layer to reduce a radial current loop size in the second electrode.

11. The implantable medical device of claim 10, wherein the second high resistance section is formed by a second gap between the third and fourth portions of the third layer, and wherein the at least one tab of the first layer extending from the second surface is positioned within the second gap.

12. A method of making an implantable medical device battery comprising:
stacking a first electrode with a second electrode, wherein the second electrode is separate from the first electrode, the second electrode including:
a first layer formed of a first material having a first continuous surface and a second continuous surface opposite the first surface, wherein the first material is a conductive material; and
a second layer positioned on the first surface of the first layer, the second layer formed of a second material different from the first material, wherein the second material is lithium, wherein the second layer includes a first portion separated from a second portion by a high resistance section, the high resistance section having a greater resistance compared to the first and second portions of the second layer to reduce a radial current loop size in the second electrode.

13. The method of claim 12, wherein the conductive material is selected from one of stainless steel and nickel.

14. The method of claim 12, further including forming the high resistance section.

15. The method of claim 14, wherein the high resistance section is a gap between the first and second portions of the second layer.

16. The method of claim 15, further including depositing an insulating material within the gap to maintain the gap between the first and second portions of the second layer.

17. The method of claim 15, wherein the first layer includes a tab extending from the first surface of the first layer, the method further includes:
positioning the tab within the gap between the first and second portions of the second layer.

18. The method of claim 17, further including coupling the tab to the first layer.

19. The method of claim 18, wherein the tab is formed of a third material that is different from the first material.

\* \* \* \* \*